United States Patent
Striano

(10) Patent No.: US 10,238,363 B2
(45) Date of Patent: Mar. 26, 2019

(54) NEEDLE GUIDE FOR ULTRASOUND TRANSDUCER

(71) Applicant: Richard D. Striano, Suffern, NY (US)

(72) Inventor: Richard D. Striano, Suffern, NY (US)

(*) Notice: Subject to any disclaimer, the term of this patent is extended or adjusted under 35 U.S.C. 154(b) by 557 days.

(21) Appl. No.: 14/825,570

(22) Filed: Aug. 13, 2015

(65) Prior Publication Data

US 2016/0051224 A1 Feb. 25, 2016

Related U.S. Application Data

(60) Provisional application No. 62/040,132, filed on Aug. 21, 2014.

(51) Int. Cl.
- *A61B 8/00* (2006.01)
- *A61B 8/12* (2006.01)
- *A61B 17/34* (2006.01)
- *A61B 90/13* (2016.01)
- *A61B 90/30* (2016.01)

(52) U.S. Cl.
CPC .............. *A61B 8/4455* (2013.01); *A61B 8/12* (2013.01); *A61B 17/3403* (2013.01); *A61B 90/13* (2016.02); *A61B 2017/3413* (2013.01); *A61B 2090/309* (2016.02); *A61B 2560/0214* (2013.01)

(58) Field of Classification Search
CPC ........................................................ A61B 8/14
USPC ......................................................... 600/461
See application file for complete search history.

(56) References Cited

U.S. PATENT DOCUMENTS

| | | | |
|---|---|---|---|
| 3,901,220 A | 8/1975 | Koyasu et al. | |
| 4,475,553 A | 10/1984 | Yamaguchi et al. | |
| 4,501,278 A | 2/1985 | Yamaguchi et al. | |
| 4,527,569 A | 7/1985 | Kolb | |
| 4,651,732 A | 3/1987 | Frederick | |
| 5,320,111 A | 6/1994 | Livingston | |
| 5,611,345 A | 3/1997 | Hibbeln | |
| 5,647,373 A * | 7/1997 | Paltieli | A61B 8/00 600/461 |
| 5,651,783 A * | 7/1997 | Reynard | A61B 1/042 606/17 |
| 5,820,623 A * | 10/1998 | Ng | A61B 34/70 318/568.11 |
| 5,924,992 A * | 7/1999 | Park | A61B 17/3403 600/461 |
| 5,930,329 A * | 7/1999 | Navab | A61B 90/36 378/98.12 |
| 5,931,787 A | 8/1999 | Dietz et al. | |
| 6,013,035 A | 1/2000 | Unger et al. | |
| 6,041,249 A | 3/2000 | Regn | |
| 6,110,112 A * | 8/2000 | Heywang-Koebrunner | A61B 17/3403 600/439 |
| 6,206,890 B1 * | 3/2001 | Truwit | A61B 90/11 600/417 |
| 6,296,614 B1 * | 10/2001 | Pruter | A61B 17/3403 600/461 |
| 6,357,890 B1 * | 3/2002 | Parsons | A44B 15/00 362/116 |
| 6,361,499 B1 | 3/2002 | Bates et al. | |

(Continued)

Primary Examiner — Tse W Chen
Assistant Examiner — Joanne M Hoffman
(74) Attorney, Agent, or Firm — Leason Ellis LLP

(57) ABSTRACT

A needle guidance apparatus is an accessory that is configured to be coupled to an ultrasound transducer probe and is configured to align and guide the placement of a needle to a target location beneath the skin of a patient.

13 Claims, 4 Drawing Sheets

(56) References Cited

U.S. PATENT DOCUMENTS

| | | | |
|---|---|---|---|
| 6,379,307 B1* | 4/2002 | Filly | A61B 8/0833 600/461 |
| 6,443,960 B1 | 9/2002 | Brabrand et al. | |
| 6,689,067 B2 | 2/2004 | Sauer et al. | |
| 6,702,749 B2* | 3/2004 | Paladini | A61B 8/0833 600/437 |
| 6,783,494 B2 | 8/2004 | Ogawa | |
| 6,847,490 B1 | 1/2005 | Nordstrom et al. | |
| 6,895,266 B1 | 5/2005 | Hollis | |
| 7,241,267 B2 | 7/2007 | Furia | |
| 7,811,265 B2 | 10/2010 | Hering et al. | |
| 7,904,138 B2* | 3/2011 | Goldman | A61B 5/0059 353/119 |
| 7,976,469 B2 | 7/2011 | Bonde et al. | |
| 8,073,529 B2 | 12/2011 | Cermak et al. | |
| 8,118,743 B2* | 2/2012 | Park | A61B 8/4422 600/437 |
| 8,162,852 B2 | 4/2012 | Norris | |
| 8,206,326 B2* | 6/2012 | Schafer | A61M 37/0092 601/1 |
| 8,257,264 B2* | 9/2012 | Park | A61B 8/0833 600/437 |
| 8,317,681 B1 | 11/2012 | Gazdzinski | |
| 8,496,593 B2 | 7/2013 | Park et al. | |
| 2002/0133079 A1 | 9/2002 | Sandhu | |
| 2003/0018265 A1 | 1/2003 | Tahara | |
| 2003/0120154 A1* | 6/2003 | Sauer | A61B 8/0833 600/459 |
| 2004/0046242 A1* | 3/2004 | Asakawa | H01L 31/0203 257/678 |
| 2005/0283059 A1* | 12/2005 | Iyer | A61B 5/14542 600/338 |
| 2007/0043291 A1* | 2/2007 | Fidel | A61B 8/12 600/439 |
| 2007/0197887 A1* | 8/2007 | Lunak | A61B 5/02055 600/323 |
| 2008/0009743 A1* | 1/2008 | Hayasaka | A61B 8/0833 600/461 |
| 2008/0108981 A1 | 5/2008 | Telfair et al. | |
| 2008/0147147 A1* | 6/2008 | Griffiths | A61B 5/0059 607/88 |
| 2009/0171219 A1 | 7/2009 | Uchibori | |
| 2010/0041990 A1 | 2/2010 | Schlitt et al. | |
| 2010/0106056 A1* | 4/2010 | Norris | A61B 8/0841 600/567 |
| 2010/0168576 A1 | 7/2010 | Poland et al. | |
| 2010/0312121 A1 | 12/2010 | Guan | |
| 2011/0251491 A1 | 10/2011 | Oonuki | |
| 2011/0282188 A1 | 11/2011 | Burnside et al. | |
| 2011/0313280 A1 | 12/2011 | Govari et al. | |
| 2011/0319759 A1 | 12/2011 | Liu et al. | |
| 2012/0165679 A1 | 6/2012 | Orome et al. | |
| 2012/0203095 A1* | 8/2012 | Krieger | A61B 5/055 600/411 |
| 2012/0310141 A1 | 12/2012 | Kornfield et al. | |
| 2013/0172962 A1 | 7/2013 | Song et al. | |
| 2014/0275971 A1* | 9/2014 | Brown | A61B 17/3403 600/414 |
| 2015/0320439 A1* | 11/2015 | Andrews | A61B 8/0841 600/461 |
| 2016/0199025 A1* | 7/2016 | Takeda | A61B 8/0841 600/424 |
| 2017/0079622 A1* | 3/2017 | O'Donnell | A61B 5/0035 |

* cited by examiner

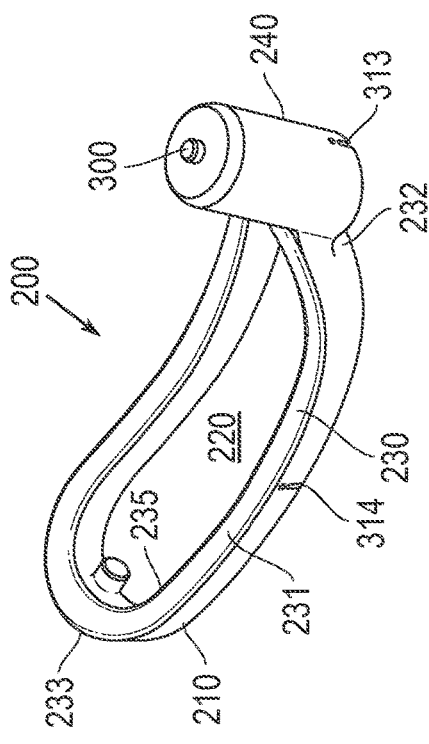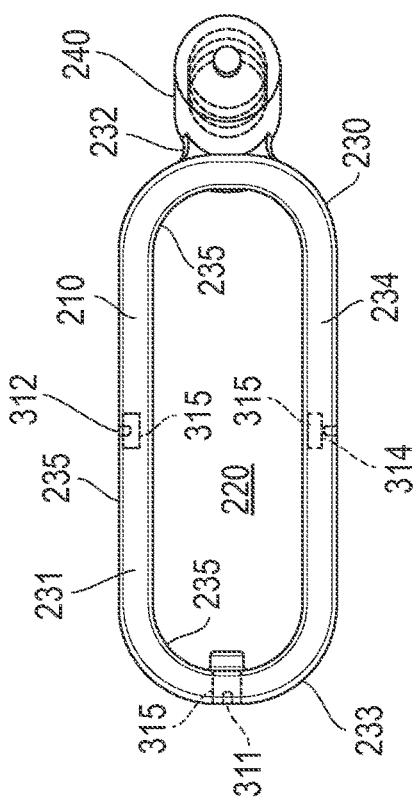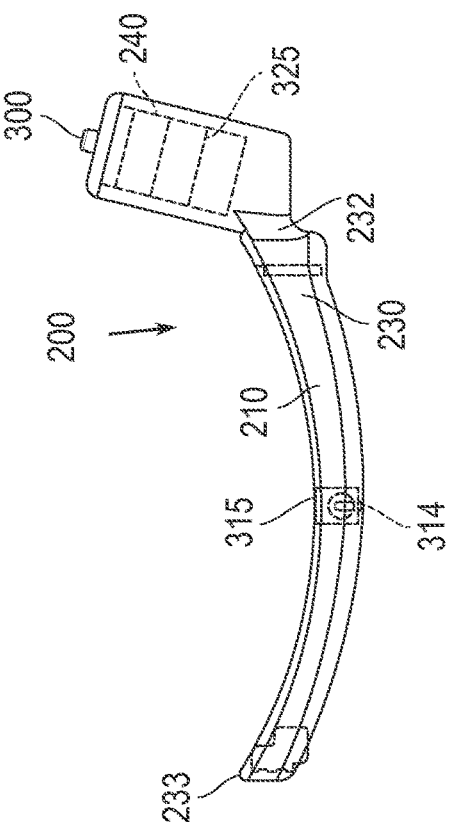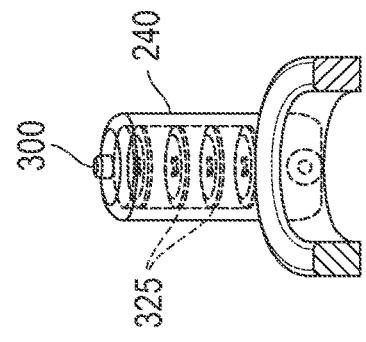

1

NEEDLE GUIDE FOR ULTRASOUND TRANSDUCER

CROSS-REFERENCE TO RELATED APPLICATION

The present application claims the benefit of U.S. patent application Ser. No. 62/040,132, filed Aug. 21, 2014, which is hereby incorporated by reference in its entirety.

TECHNICAL FIELD

The present invention is directed to sonography equipment and more particularly, is related to an accessory that is coupled to an ultrasound transducer probe and is configured to align and guide the placement of a needle to a target location beneath the skin of a patient using an ultrasound system.

BACKGROUND

Medical sonography is a diagnostic medical imaging method used for the visualization of soft tissue, such as muscles, tendons and internal organs. This type of technology is commonly understood to be safer, less expensive and more portable compared to other diagnostic imaging techniques, such as magnetic resonance imaging (MRI) or computed tomography (CT).

Compared to other prominent methods of medical imaging, ultrasonography (ultrasound) has several advantages. Unlike other imaging techniques, ionizing radiation is not a component of sonography and so poses no known risks to the patient. In addition, it provides images in real-time (rather than after an acquisition or processing delay), it is portable and can be brought to a patient's bedside, and it is substantially lower in cost. Drawbacks of ultrasonography include various limits on its field of view including difficulty imaging structures behind bone, and its relative dependence on a skilled operator. Ultrasound is also increasingly being used in trauma and by EMT response teams.

The non-invasive and portable nature of an ultrasound exam provides immediate results that are nearly as informative as other imaging exam methods. Further, ultrasound guided needle placement has allowed clinicians to perfect regional anesthesia procedures, needle biopsies, central line placement, and other procedures. Injections of cortisone, platelet rich plasma, hyaluronic acid supplements and local anesthetics provide pain relief and healing benefits through accurately place injections.

Using ultrasound to view a needle to accurately place an injection greatly increases the rate of successful placement of the medicament. Though a variety of techniques are used to track the path of the needle, from mechanical to magnetic, most require specialized probes and needles, the placing of markers, calibration, and a certain amount of pre-procedure setup. Finding a needle tip during an ultrasound procedure can be technically challenging and this is particularly true with out of plane needle insertion techniques in which the needle is inserted into the patient outside of the plane of the ultrasound transducer (probe). When a needle is inserted out of plane with the transducer (probe), there are a number of reasons that the needle image is not seen. For example, the needle image may not be seen because: (1) the transducer is still far away from the needle and thus, the beam from the transducer (probe) is not crossing the needle or (2) the beam hitting the needle is deflected away from the transducer and not returning to the transducer because of the angle of incidence (e.g., the angle is less than 90 degrees). One of the techniques (maneuvers) that can be used to increase needle visibility in the ultrasound is to move the transducer (probe) towards the needle tip and then away from the needle tip (i.e., the transducer can be pivoted while positioned on the body). This movement determines whether any observed spot on an ultrasound is a shaft or the tip of the needle.

There is therefore a need for a simple, effective method for tracking the needle as it is advanced in the body towards the target tissue.

SUMMARY

In accordance with the present invention, a needle guidance apparatus (guide) is provided for use with an ultrasound imaging device that generates a substantially planar ultrasound beam from a distal end of a transducer probe. The needle guidance apparatus includes a frame having a central opening for receiving the distal end of the transducer probe such that the distal end of the transducer probe extends below the frame for placement against skin of a patient. The frame is configured to be detachably coupled about an outer surface of the transducer probe. The needle guidance apparatus includes a plurality of illumination slits formed in the frame. The illumination slits are spaced apart from one another and are open along an outer surface of the frame so as to face outward away from the frame. The needle guidance apparatus also includes a light source in communication with the plurality of illumination slits so as to project light through the illumination slits in a direction outwardly away from the frame. The light source is oriented relative to the plurality of illumination slits such that a pattern of light is formed on the skin for guiding placement of a needle. An actuator and a power source are operatively connected to the light source for controlling operation of the light source.

In another aspect, the present invention provides a method for delivering a needle to a target location in a guided manner using an ultrasound imaging device that generates a substantially planar ultrasound beam from a distal end of a transducer probe comprising the steps of: (1) attaching a needle guidance apparatus to the transducer probe; (2) actuating the needle guidance apparatus to cause a plurality of visible beams of light to be projected radially outward from the needle guidance apparatus onto skin of the patient; wherein the visible beams define and extend along first and second light axes that are orthogonal to one another; (3) positioning the needle along one of the first and second light axes that is visible along the skin of the patient and advancing the needle into skin; and (4) moving the transducer probe with the needle guidance apparatus coupled thereto until the other of the first and second light axes that is visible along the skin of the patient intersects the needle that is inserted into the patient which is indicative that an angle of incidence between the needle and the planar ultrasound beam is such that the needle will be visible on a display associated with the ultrasound imaging device. In one exemplary embodiment, the angle of incidence is about 90 degrees.

BRIEF DESCRIPTION OF THE DRAWING FIGURES

FIG. 3 is a top perspective view of the alignment guide;

FIG. 5 is a top plan view of the alignment guide;

FIG. 6 is a side elevation view of the alignment guide; and

FIG. 7 is an end view of the alignment guide.

DETAILED DESCRIPTION OF CERTAIN EMBODIMENTS

Figure 1:
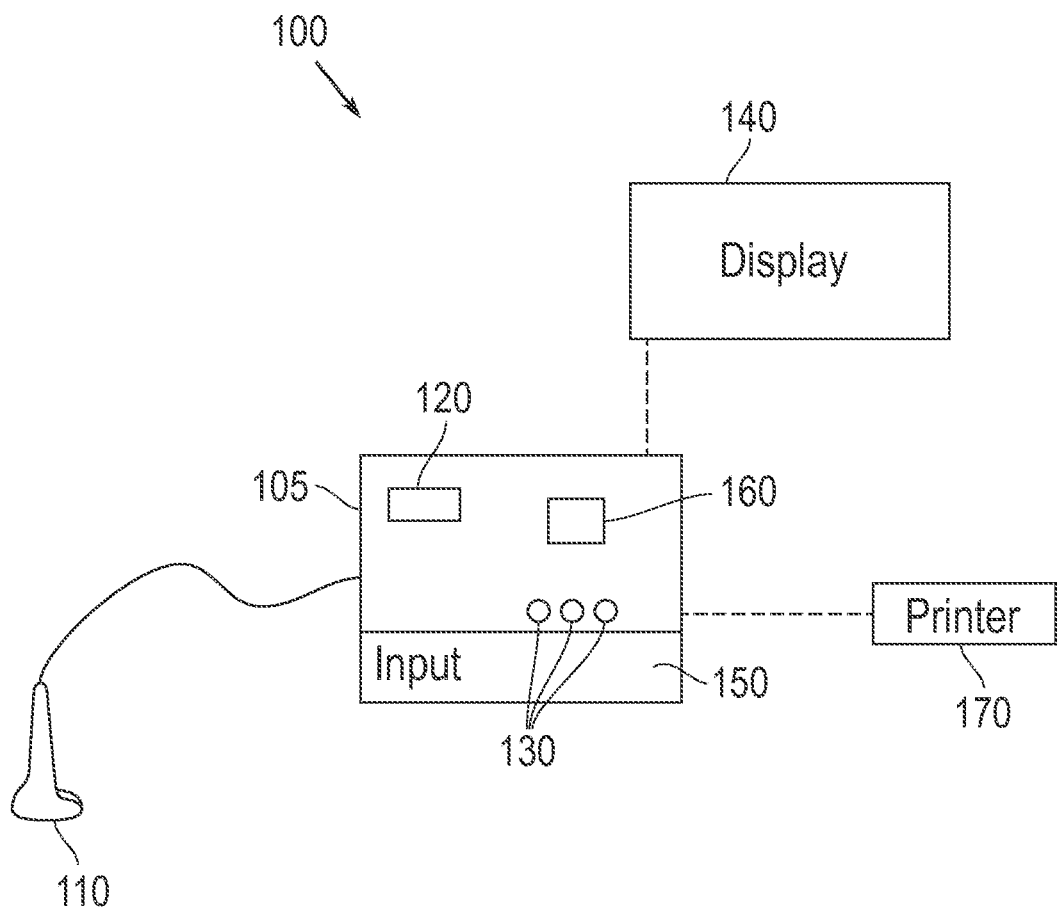
FIG. 1 is a schematic of an ultrasound system (ultrasound imaging device)

FIG. 1 illustrates a traditional ultrasound system (ultrasound imaging device) 100. The ultrasound system 100 includes a transducer probe 110 that sends and receives sound waves; a central processing unit (CPU) 120 (which can be computer or the like, shown generally at 105, that performs calculation and contains the electrical power supplies for itself and the transducer probe 110); transducer pulse controls 130 (changes the amplitude, frequency and duration of the pulses emitted from the transducer probe); a display 140 (which displays the image from the ultrasound data processed by the CPU 120; an input device 150 (e.g., a keyboard/cursor for inputting data and taking measurements from the display 140); storage 160 for storing the acquired images; and a printer 170 for printing images from the displayed data. It will be appreciated that the aforementioned elements are merely exemplary and the system 100 can include more or less elements.

The transducer probe 110 is the main part of the ultrasound device 100. The transducer probe 110 generates the sound waves and receives the echoes (i.e., the transducer probe 110 generates an ultrasound beam 20 which is a planar beam that is vertically oriented in FIG. 2). As is known, the transducer probe 110 generates and receives sound waves using a principle called the piezoelectric (pressure electricity) effect. In the transducer probe 110, there are one or more quartz crystals called piezoelectric crystals. When an electric current is applied to these crystals, they change shape rapidly. The rapid shape changes, or vibrations, of the crystals produce sound waves that travel outward. Conversely, when sound or pressure waves hit the crystals, they emit electrical currents. Therefore, the same crystals can be used to send and receive sound waves. The transducer probe 110 also has a sound absorbing substance to eliminate back reflections from the probe 110 itself, and an acoustic lens to help focus the emitted sound waves.

Transducer probes 110 come in many shapes and sizes. The shape of the probe 110 determines its field of view, and the frequency of emitted sound waves determines how deep the sound waves penetrate and the resolution of the image. Transducer probes 110 can contain one or more crystal elements; in multiple-element probes, each crystal has its own circuit. Multiple-element probes have the advantage that the ultrasonic beam can be "steered" by changing the timing in which each element gets pulsed; steering the beam is especially important for cardiac ultrasound. In addition to probes that can be moved across the surface of the body, some probes are designed to be inserted through various openings of the body (vagina, rectum, esophagus) so that they can get closer to the organ being examined (uterus, prostate gland, stomach); getting closer to the organ can allow for more detailed views.

The CPU 120 is the brain of the ultrasound machine. The CPU 120 is basically a computer that contains the microprocessor, memory, amplifiers and power supplies for the microprocessor and transducer probe 110. The CPU 120 sends electrical currents to the transducer probe to emit sound waves, and also receives the electrical pulses from the probes that were created from the returning echoes. The CPU 120 does all of the calculations involved in processing the data. Once the raw data are processed, the CPU 120 forms the image on the monitor. The CPU 120 can also store the processed data and/or image on disk.

It will also be appreciated that there are continues advancements in this field and in particular, the traditional ultrasound machines present a two-dimensional image, or "slice," of a three-dimensional object (fetus, organ); however, there are at least two other types of ultrasound that are currently in use, namely, 3-D ultrasound imaging and Doppler ultrasound.

As mentioned herein, there are many different uses for ultrasound equipment that span many different medical fields (practices) including but not limited to obstetrics and gynecology; cardiology; urology and as described herein, ultrasound is also used to guide a needle to a target location to allow a biopsy to be performed and/or to deliver medication, etc.

Figure 2:
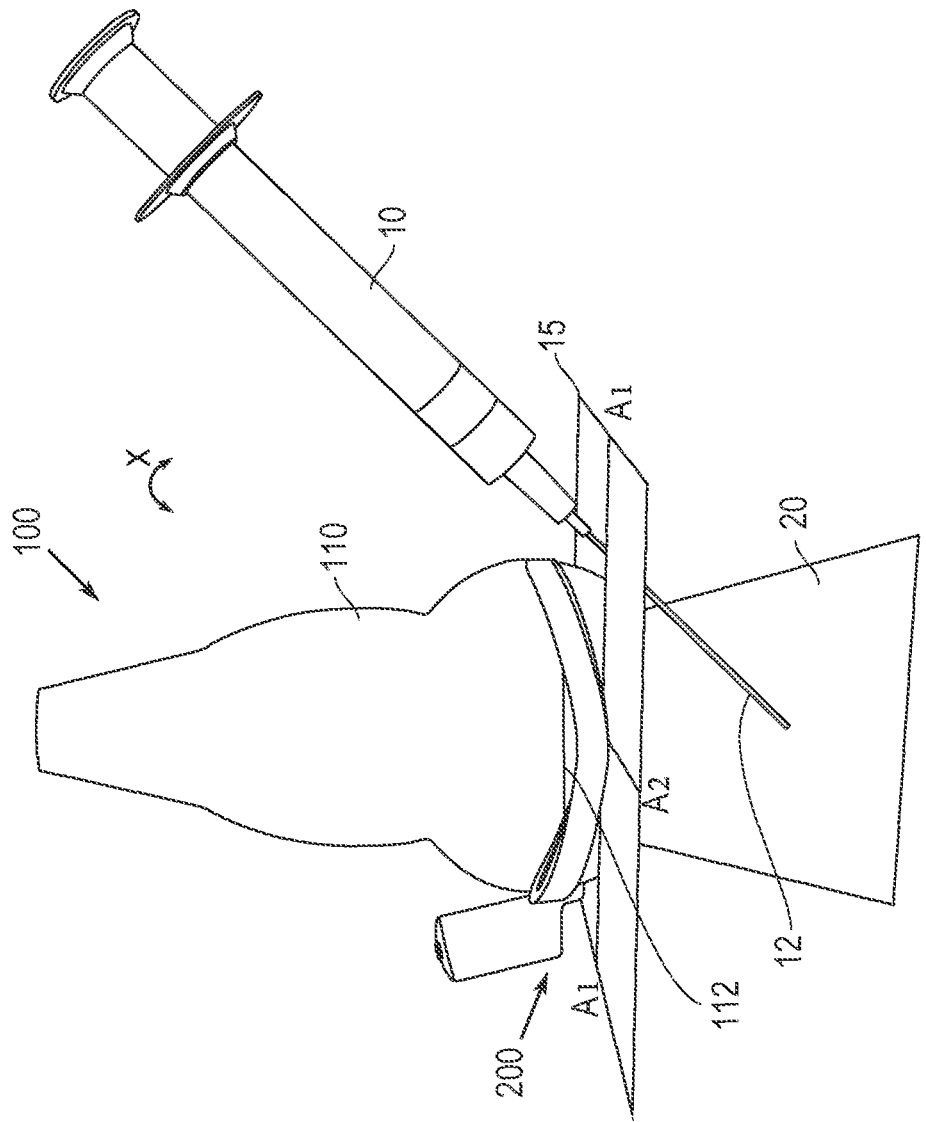
FIG. 2 is side perspective view of an alignment guide (needle guidance apparatus) in accordance with the present invention being coupled to a transducer probe, with two axes of illumination being shone on the top surface of the patient's skin to guide a needle to a target location for placement.
Figure 4:
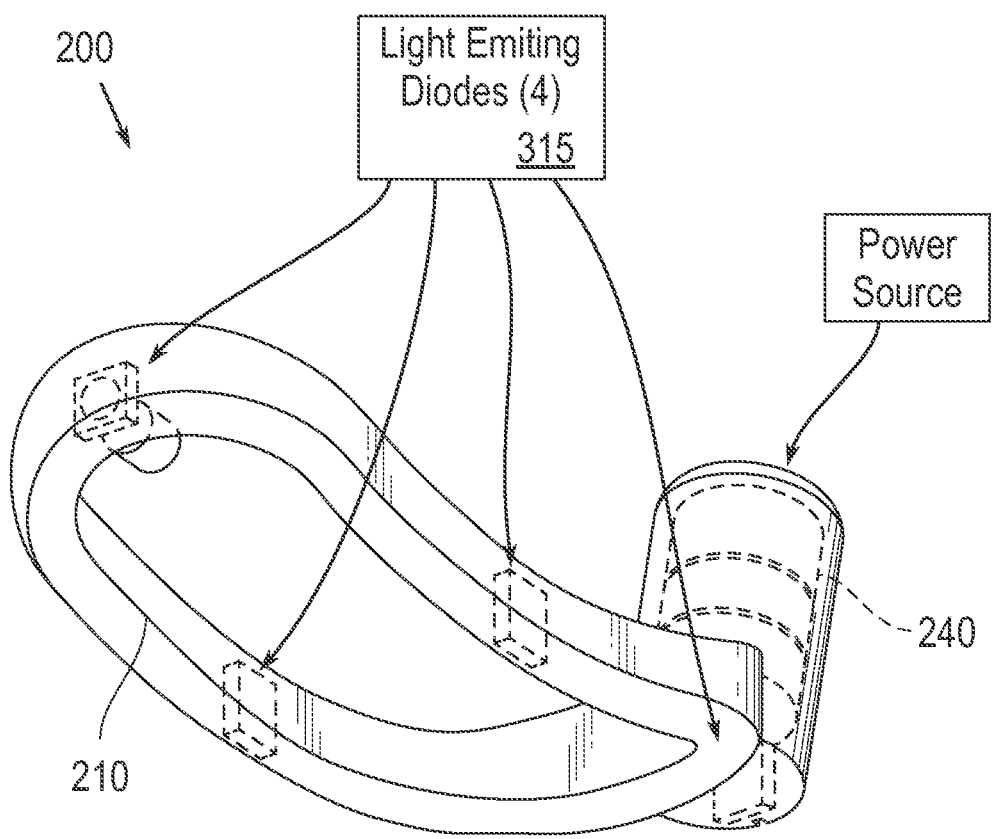
FIG. 4 is a bottom perspective view of the alignment guide.

FIG. 2 shows a traditional use of the ultrasound probe 110 on the skin 15 of a patient. In this exemplary application, the ultrasound probe 110 is used to guide placement of a needle 10 to a target location (i.e., target tissue location) for injecting an agent through a sharp distal needle tip 12. Alternatively, the needle 10 can be used to perform a biopsy at the target location. As discussed herein, the guide 200 is for needle alignment and needle guidance underneath the patient's skin 15.

The imaging (scan) plane (beam plane) of the ultrasound probe 110 is shown at 20.

In accordance with the present invention and as shown in FIGS. 2-7, an accessory 200 is provided for use with the transducer probe 110 and is configured to provide alignment and guidance of an object, such as a needle that is advanced within the patient. The accessory 200 is configured to mate with transducer probes from a wide variety of different suppliers and therefore, the accessory 200 can provided and supplied separate from the transducer probe 110 and the ultrasound system 100. The accessory 200 will also be referred to herein as a guide 200 or a needle guidance apparatus 200 or needle guide unit 200.

FIG. 2 shows the needle guidance apparatus/guide 200 being coupled to the ultrasound probe 110.

The guide 200 is formed of a body (frame) 210 that is configured to mate with the transducer probe 110 in such a way that the guide 200 can be easily removed from a distal end 112 of the transducer probe 110 and attached back to when desired. For example, if cleaning or maintenance of the guide 200 is desired, the guide 200 is simply removed from the distal end 112 of the transducer probe 110. The body 210 thus includes a central opening 220 into which the distal end 112 of the transducer probe 110 is seated. Since most transducer probes 110 have an oblong shape, the body 210 has a complementary shape as shown.

The body 210 has two distinct sections, namely a first section 230 that receives and surrounds a portion of the transducer probe 110 (and includes the opening 220) and a second section 240 that houses the electronics and/or power supply of the guide 200. The second section 240, which can be thought of as a housing, is integrally formed with the first section 230 and merely extends outwardly therefrom so as to be disposed external to the transducer probe 110. In the illustrated embodiment, the body 210 has two opposing first and second ends 232, 233 and two opposing sides 234, 235 that extend between the ends 232, 233. The first section 230 of the body 210 is a continuous wall or rail structure 231 that has an annular shape defined by the central opening 220. The wall 231 of the first section 230 thus extends completely around the opening 220 (thereby defining it) and when the transducer probe 110 is inserted into the opening 220, the first section 230 mates with and is disposed about the outer surface of the probe 110. The first section 230 can be held about the distal end 112 of the probe 110 by a mechanical fit, such as a frictional fit, or by using other mechanism, such as adjustable fasteners, etc.

Since the outer surface of the transducer probe 110 is curved, inner surfaces 235 of the wall 231 of the first section 230 that defines the opening 220 are likewise curved and preferably smooth. The opening 220 also has an oblong shape defined by the wall 231 of the first section 230.

In accordance with the present invention, the guide 200 includes a light feature that assists the user in the ultrasound procedure and more specifically, to guide the placement of a needle to the target location for injection or biopsy. More specifically, the light feature includes a light source that is configured to emit light at strategic places and in particularly, there is a plurality of light features that are disposed about the wall 231. In the illustrated embodiment, there are four light features that are arranged in two pairs with each light feature of the pair being directly opposite the other. In other words, the four light features are arranged 90 degrees apart. Each light feature includes an opening or slit that is formed in the wall 231 that opens outwardly. More specifically, the guide body includes a first slit 311, a second slit 312, a third slit 313 and a fourth slit 313. The slits 311, 312, 313, 314 are formed in the wall 231 such that light passes therethrough and is directed outwardly onto the skin of the patient. The slits 311, 312, 313, 314 are thus illumination slits that project light onto the tissue of the patient. The transducer probe 110 in no way interferes with said projection since the slits 311, 312, 313, 314 are disposed about the outer surface (exterior) of the transducer probe 110.

It will be appreciated that the first and third slits 311, 313 are aligned along a first axis (A1) and the second and fourth slits 312, 314 are aligned along a second axis (A2) as shown in FIG. 2. The first and second axes (A1) and (A2) intersect one another since they are perpendicular to one another and preferably, the first and second axes intersect one another at a central location of the body and centrally within the opening 220. The light projects outwardly through the four slits to create an illumination pattern on the skin of the patient. In the illustrated embodiment, the light pattern is in the form of four light markings that is similar to cross-hair markings with the exception that the light is only projected outwardly from the guide body and does not extend into the opening 220 in which the transducer probe 110 is located.

Any number of different light sources 315 can be used in the present invention and it will be understood that it is within the scope of the present invention that the guide 200 includes a single light source 315 that is configured to project light through all of the slits 311, 312, 313, 314 or there can be a plurality of separate light sources 315. For example, there can be four light sources 315 such that each slit 311, 312, 313, 314 has its own associated light source 315. The light sources 315 can be compact, low voltage light sources, such as light emitting diodes (LEDs). The light sources 315 are all operatively connected to common electronics, such as a controller/processor, that allows the light sources 315 to be actuated at the same time. The light sources 315 are also operatively connected to a common power supply 325 (e.g., battery) for powering thereof. As best shown in FIGS. 6 and 7, the power source 325 can be in the form of a small watch battery, such as CR2032.

In the illustrated embodiment, the slits 311, 312, 313, 314 are vertically oriented rectangular shaped slits. It will be appreciated that the slits 311, 312, 313, 314 can take any number of different forms so long as they project light in a linear manner and in a direction away from the body of the guide 200. Each light projection axis (A1, A2) is oriented normal to the body of the guide 200, thereby resulting in the four light projections being oriented 90 degrees apart from one another.

The second section 240 is formed at the first end 232 and can be in the form of a housing or casing that contains the electronics and power supply. In the illustrated embodiment, the second section 240 is in the form of cylindrical housing that is vertically oriented relative to the first section 230. The second section 240 can thus contain a battery that is used to power the light sources 315. The electronics also include an actuator 300 that is used to turn on the light sources 315 to project the light through the four slits 311, 312, 313, 314. The actuator 300 can be in the form of a switch, button or the like that can be easily manipulated by the user to cause the operation of the light sources 315 (i.e., turn on and turn off the light sources). In the illustrated embodiment, the actuator 300 is in the form of a button located along the top of the cylindrical housing. The actuator 300 can be a simple one press button in which pressing the button 300 once causes the light sources 315 to turn on and light projects through the four slits 311, 312, 313, 314. To shut off the guide 200, the actuator 300 is pressed again.

In accordance with the present invention, the guide 200 provides a means for guiding (aligning) a needle as it is delivered to the target site (target tissue) such that the transducer probe 110 can be placed in a position relative to the needle 10 that results in the beam being at or closer to a 90 degree angle of incidence which results in the needle 10 being within the plane of the ultrasound beam and thus visible on the display.

As mentioned herein, if the needle 10 is inserted out of plane with the transducer probe 110, the needle image may not be seen as a result of the beam hitting the needle 10 being deflected away from the transducer probe 110 and not returning to the transducer probe 110 because of the angle of incidence (e.g., less than 90 degrees). To find the needle, the user can pivot the transducer probe 110 by rocking it back and forth on the skin in order to get the emitted beam closer to a 90 degree angle of incidence. While this technique can assist the user in finding the needle 10 on the display, it is still more of a trial and error type technique in that the user simple keeps pivoting the transducer probe 110 until increased visibility of the needle 10 is achieved.

The guide 200 of the present invention overcomes the disadvantages associated with the above conventional technique and provides clear, repeatably guidance to the user. The guide 200 is first coupled to the transducer probe 110 by inserting the distal end 112 of the transducer probe 110 into the opening 220 such that the distal end 112 extends slightly below the bottom of the guide 200 to allow the transducer probe 110 to be placed in contact with the skin of the patient. The guide 200 does not impede movement of the transducer probe 110 along the skin of the patient and thus, the transducer probe 110 can be pivoted or otherwise moved along the skin.

Once the guide 200 is coupled to the transducer probe 110, the ultrasound procedure begins by first activating the actuator 300 (e.g., pressing the actuator 300) which causes light to pass through the slits 311, 312, 313, 314 onto the skin of the patient, thereby resulting in four light marks (visual linear marks) (projected LED lines) being displayed on the skin of the user. These four lines are located 90 degrees relative to one another and define the two axes A1 and A2 as discussed herein.

Next, the needle 10 is inserted into the tissue at a location spaced from the transducer probe 110 and guide 200 (i.e., at a location which is out of the plane of the transducer probe). The needle 10 is preferably inserted into the tissue at a location which lies along one of the light marks that are present along the skin of the patient. In the illustrated embodiment, the needle 10 passes through the light mark that is formed by light passing through the slit 311. It will be understood that the needle 10 can be placed on any of the other three light marks defined by light passing through one of the slits 312, 313, 314. In the present illustrated example, the needle 10 is thus located along the first axis A1 which is defined by the two light marks formed by light passing through the slits 311, 313.

The needle 10 enters the tissue at a measurable angle which will vary depending upon the location of the target tissue location to which the tip of the needle is delivered. For example, the needle 10 may enter at a steep trajectory or the needle 10 may enter at a shallower trajectory.

In order to optimize needle guidance and alignment and optimize the visibility of the needle 10 in the display 140, the transducer probe 110 is moved (pivoted) along the skin to cause the position of the transducer probe 110 to change relative to the skin. The user moves (pivots) the transducer probe 110 along the skin in a direction that causes the light marks that define the second axis A2 (i.e., the two light marks defined by the light emitted through the slits 312, 314) to move (change position) along the tissue. It will be appreciate that since the guide 200 is directly attached to the transducer probe 110, the movement (i.e., pivoting) of the transducer probe 110 is directly translated into movement of the guide 200 and since the guide 200 carries the light source (LEDs), the light marks defined by the light emitted through the slits 311, 312, 313, 314 likewise move along the tissue as the guide 200 moves.

Since the needle 10 is located at a point along the first axis A1, pivoting of the transducer probe 110 in the direction X (FIG. 2) causes the two light marks defining the second axis A2 to move in a direction either way from the needle (i.e., the needle entry point) or in a direction toward the needle (needle entry point). In accordance with the present invention, the transducer probe 110 is piloted in a direction that causes the light marks the define the second axis A2 to move toward the needle 10 (i.e., the needle entry point along the first axis A1). More specifically, the transducer probe 110 is pivoted until the second axis A2 intersects the needle 10 (needle entry point). When the second axis A2 intersects the needle 10 (needle entry point), the transducer probe 110 is at a position such that the angle of incidence between the plane of the transducer probe 110 and the needle is substantially about 90 degrees. As mentioned herein, when the angle of incidence is 90 degrees, visibility of the needle 10 on the display is optimized since the beam hitting the needle is returned to the transducer probe 110, thereby resulting in the needle being clearly displayed on the display 140.

In accordance with the present invention, sonography alignment illumination is accomplished with an enclosure that engages with a sonography device. The enclosure includes a power source, light sources, and light projection to the patient's skin surface. The power source 325 can include a number of coin style batteries (e.g., CR2032). Compact, low voltage light sources, such as light emitting diodes 315 (LEDs) shine through an array slits intended to form a pattern on the patient's skin surface to guide the placement of a needle to the location for injection.

The needle guidance apparatus 200 can be formed of any number of suitable materials, such as plastics; however, other materials, such as metal can be used.

The visible light pattern that is projected onto the skin of the patient can also be used for other purposes such as serving as a guide for placing physical markings on the skin of the patient. Since the projected light beams are formed along two axes that are orthogonal, the user can use these visible light beams to trace physical markings on the skin of the patient. For example, a marker or the like can be used to draw four physical lines on the skin of the patient. Once the transducer probe 110 and the guide 200 are removed, the user can complete and connect the four lines to form a cross-hair defined by two axes that intersect one another and are orthogonal to one another. The point of intersection of the two axes defines the center of the location at which the transducer was placed and thus, should represent a point that is directly above the target tissue. These visible, physical markings can be used by the user or others (physician) in other procedures.

In yet another aspect, the guide 200 includes certain alignment marks to assist in alignment and centering. In particular, a feature of the accessory (guide 200) is centering. That is when there is a foci of interest on a patient be it a tendon, joint space or cyst, it is desirable to center the guide 200. When the target is located at the center of the transducer probe 110, the target is also exactly centered on the screen (display 140). Therefore, when the needle 10 enters the patient at the center of the transducer probe 110, it is immediately correctly aligned so it will be advanced directly into the target without having to make corrections in the plane of advance.

As shown in FIG. 3, the body of the guide 200 can include a number of visual aids beyond the slits 311, 312, 313, 314. For example, the guide 200 can include visual marks 319 that are located above the slits 311, 312, 313, 314. The marks 319 can be dot shaped marks that serve as center alignment dots in a case where the device (guide 200) may not be turned on. Each lighted slit 311, 312, 313, 314 also serves to "center" the transducer probe 110 directly over the target. This "centering" feature for aligning the target at the center of the transducer probe 110 and the center of the screen (display 140) is independent of guiding the needle 10. For example and as mentioned herein, the skin can be marked by tracing the lighted lines to exact the location of the point of interest below the skin as visualized on the screen on the patient, and a scalpel can be used to surgically excise a target accurately in which case guiding needle 10 wouldn't even be part of the procedure. The centering can also be used to mark the location of a target to be visualized again at a later date without having to explore to find it, or in some cases to see if the lesion is still existing at a later post-surgical time.

Having described preferred embodiments of the systems and the devices (printers) (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims.

What is claimed is:

1. A needle guidance apparatus for use with an ultrasound imaging device that generates a substantially planar ultrasound beam from a distal end of a transducer probe comprising:
   a frame having a central opening for receiving the distal end of the transducer probe such that the distal end of the transducer probe extends below the frame for placement against skin of a patient, the frame being configured to be detachably coupled about an outer surface of the transducer probe;
   a plurality of illumination slits formed in the frame, the illumination slits being spaced apart from one another and are open along an outer surface of the frame so as to face outward away from the frame;
   a light source in communication with the plurality of illumination slits so as to project light through the illumination slits in a direction outwardly away from the frame, wherein the light source is oriented relative to the plurality of illumination slits such that a pattern of light is formed on the skin for guiding placement of a needle; and
   an actuator and a power source that are operatively connected to the light source for controlling operation of the light source;
   wherein the plurality of illumination slits comprises four illumination slits that are arranged in two pairs;
   wherein the frame has an oblong shape defined by opposite first and second ends and first and second opposite sides that extend between the first and second ends, wherein a first illumination slit is formed at the first end, a second illumination slit is formed at the opposite second end, a third illumination slit is formed along the first side, and a fourth illumination slit is formed along the second side;
   wherein the first, second, third and fourth illumination slits are positioned about 90degrees apart from one another such that a first axis (A1) passes through the first and third slits and a second axis (A2) passes through the second and fourth slits.

2. The needle guidance apparatus of claim 1, wherein the frame has an oblong shape that is configured to surround the transducer probe and be frictionally coupled thereto.

3. The needle guidance apparatus of claim 1, wherein the light source comprises a plurality of light sources with each illumination slit having one light source that is positioned adjacent thereto so as to emit light through the illumination slit.

4. The needle guidance apparatus of claim 3, wherein the plurality of light sources comprises low voltage light sources.

5. The needle guidance apparatus of claim 4, wherein the low voltage light sources comprise LEDs.

6. The needle guidance apparatus of claim 1, wherein the pattern of light comprises a plurality of straight beams of light that are visible on the skin of the patient.

7. The needle guidance apparatus of claim 6, wherein there are four beams of light that are projected from the frame and visible along the skin of the patient.

8. The needle guidance apparatus of claim 1, wherein the actuator comprises a switch for turning the light source on and off.

9. The needle guidance apparatus of claim 1, wherein the power source comprises one or more batteries.

10. The needle guidance apparatus of claim 1, wherein the actuator and power source are contained within a housing that is integrally formed with the frame and is located at one end thereof.

11. A needle guidance apparatus for use with an ultrasound imaging device that generates a substantially planar ultrasound beam from a distal end of a transducer probe comprising:
    a frame having a central opening for receiving the distal end of the transducer probe such that the distal end of the transducer probe extends below the frame for placement against skin of a patient, the frame being configured to be detachably coupled about an outer surface of the transducer probe, the frame having a continuous side wall that terminates in a bottom edge that faces the distal end of the transducer probe;
    a plurality of illumination slits formed in the side wall of the frame, the illumination slits being spaced apart from one another and are open along an outer surface of the frame so as to face outward away from the frame, wherein at least two of the plurality of illumination slits are positioned such that the transducer probe is disposed between the at least two of the plurality of illumination slits, the at least two of the plurality of illumination slits facing in opposite directions from one another;
    a light source in communication with the plurality of illumination slits so as to project light through the illumination slits in a direction outwardly away from the frame, wherein the light source is oriented relative to the plurality of illumination slits such that a pattern of light is formed on the skin for guiding placement of a needle; and
    an actuator and a power source that are operatively connected to the light source for controlling operation of the light source
    wherein the frame has an oblong shape defined by opposite first and second ends and first and second opposite sides that extend between the first and second ends, wherein a first illumination slit is formed at the first end, a second illumination slit is formed at the opposite second end, a third illumination slit is formed along the first side, and a fourth illumination slit is formed along the second side;
    wherein the first, second, third and fourth illumination slits are positioned about 90 degrees apart from one another such that a first axis (A1) passes through the first and third slits and a second axis (A2) passes through the second and fourth slits.

12. The needle guidance apparatus of claim 11, wherein the plurality of illumination slits comprises four illumination slits that are arranged in two pairs.

13. The needle guidance apparatus of claim 11, wherein the first and second axes (A1, A2) intersect one another at a center point of the opening.

* * * * *